United States Patent [19]

Wells

[11] Patent Number: 5,759,178

[45] Date of Patent: Jun. 2, 1998

[54] CANNULA TIP

[76] Inventor: John Wells, 8000 S. Kolb Rd., Tucson, Ariz. 85706

[21] Appl. No.: 697,142

[22] Filed: Aug. 20, 1996

[51] Int. Cl.$^6$ .................................................. A61M 5/00
[52] U.S. Cl. ........................ 604/240; 604/187; 604/264; 604/272
[58] Field of Search ..................... 604/240, 187, 604/269, 272; 285/390, 355, 501

[56] References Cited

U.S. PATENT DOCUMENTS

| | | | |
|---|---|---|---|
| 3,278,357 | 10/1966 | Getting et al. | 604/240 |
| 4,878,904 | 11/1989 | Callaway | 604/272 |
| 5,002,538 | 3/1991 | Johnson | 604/240 |

*Primary Examiner*—Michael Buiz
*Assistant Examiner*—Daphna Shai

[57] ABSTRACT

An improved cannula with needle which provides improved support between the cannula and the syringe. The cannula provides a base member which is substantially perpendicular to the wall member forming the edge of the barrel. In this manner, lateral forces applied to the barrel of the syringe are efficiently transferred to the cannula without causing undue force upon the syringe's nozzle or the side portion of the barrel wall. Further, the cannula attaches to the outside of the syringe nozzle. Preferably, this attachment is accomplished by a thread which engages the exterior of the nozzle as the cannula is twisted onto the nozzle. Another embodiment of the invention allows the needle portion to be attached to the nozzle through a luer-lock arrangement and then the support member applied over the needle arrangement. Still another embodiment creates a locking mechanism to the nozzle which is secured both at the inside and the outside of the nozzle.

26 Claims, 2 Drawing Sheets

CANNULA TIP

BACKGROUND

This invention relates generally to medical instruments and more particularly to cannulas used with syringes.

While typical use of a syringe does not place undue forces upon the needle and its luer-lock fastener's connection to the syringe, there are many applications which apply a great deal of force and torque. This force, if used on a traditional needle, can break the nozzle of the syringe, thereby contaminating the area and possibly injuring the patient.

To strengthen this connection, a variety of techniques have been tried including those described in: U.S. Pat. No. 4,932,945, entitled "Disposable Shielded Catheter-Cannula Insertion Needle" issued to Braginetz et al. on Jun. 12, 1990; U.S. Pat. No. 4,784,156, entitled "Cannula Including a Valve Structure and Associated Instrument Elements and Method for Using Same" issued to Garg on Nov. 15, 1988; U.S. Pat. No. 4,758,225, entitled "Devices for Sampling, Drainage or Infusion of Liquids from or to the Human or Animal Body" issued to Cox et al. on Jul. 19, 1988; and, U.S. Pat. No. 5,002,538, entitled Syringe Adapter and Method" issued to Johnson on Mar. 26, 1991.

All of these attempts suffer from a variety of problems which are exemplified by the Johnson device. The Johnson device attempts to buttress the syringe by providing a cannula which surrounds the barrel of the syringe. The theory is that the now buttressed barrel/shoulder intersection will withstand the torque which being applied.

Unfortunately, this brute force approach to the problem hides the end of the syringe barrel so that the user is unable to monitor the preliminary aspiration. This "blind spot" created by the Johnson apparatus is a significant hinderance to the physician.

The Johnson solution further transfers the forces directly against the side wall of the syringe. This perpendicular force to the side wall easily punctures the wall.

For many of the apparatus which have been developed to solve this problem, attachment to the syringe is through a traditional luer-lock. The narrow tunnel created by the barrel which the luer-lock attaches, becomes extremely fragile and tends to crack or break during the manual stresses applied by the surgeon during use in such arduous tasks as liposuction.

It is clear that there is a need for an improved cannula.

SUMMARY OF THE INVENTION

The invention is an improved cannula with needle which provides improved support between the cannula and the syringe. The support is important for a variety of applications including such areas as liposuction where a large amount of torque is applied to the needle during the operation.

The syringe is constructed of a side wall member which forms the barrel of the syringe. At one end of the barrel is a shoulder which extends to the nozzle portion. The nozzle has a channel which communicates with the barrel. A plunger extends down the barrel to either force liquid from, or draw liquid into, the barrel.

The cannula provides a base member which is substantially perpendicular to the wall member forming the edge of the barrel. In the preferred embodiment of the invention, the base member is substantially circular and has a diameter slightly greater than the barrel.

Lateral movement to the cannula is transmitted directly against the longitudinal length of the barrel's wall. This force transference capitalizes upon the natural strength of the wall member whereas the prior art applied the torque pressure perpendicular to the wall itself.

In this manner, lateral forces applied to the barrel of the syringe are efficiently transferred to the cannula without causing undue force upon the syringe's nozzle.

This transference of the pressure along the wall's longitudinal axis effectively uses the entire length of the wall as a bracing member. Energy, whether coming through the syringe into the cannula or vice versa, is effectively and harmlessly transmitted along the wall. No force is applied which attempts to puncture or pierce the wall member of the syringe.

Further, the cannula attaches to the outside of the syringe nozzle. Preferably, this attachment is accomplished by a thread which engages the exterior of the nozzle as the cannula is twisted onto the nozzle.

The outside of the nozzle provides an exceptionally durable securing mechanism which in conjunction to the cannula's base member's pressing through the syringe's shoulder and against the wall member, minimizes any torquing forces which may be applied against the nozzle. The nozzle, in this way, provides for exceptional gripping power without worry of failure due to stressing (through a torque between the cannula and the syringe) during use.

To provide an even more secure attachment between the cannula and the syringe, another embodiment of the invention allows the needle portion to be attached to the nozzle through a luer-lock arrangement and then the support member of the cannula applied over the needle arrangement.

In this manner, the surgeon is able to use a variety of needles and simply apply the support over the needle to obtain the mechanical support required for the specific operation.

Still another embodiment creates a locking mechanism to the nozzle which is secured both at the inside and the outside of the nozzle.

This embodiment of the invention has exceptional gripping power since the nozzle of the syringe is actually compressed between the two locking mechanisms (the outer thread and an inner luer-lock arrangement).

The invention, together with various embodiments thereof, will be more fully explained by the attached drawings and the following descriptions.

DRAWINGS IN BRIEF

FIG. 1 is a side view of the preferred embodiment in conjunction with a syringe.

FIGS. 2A, 2B, and 2C are front, side, and end views respectively of the preferred embodiment.

DRAWINGS IN DETAIL

Figure 1:
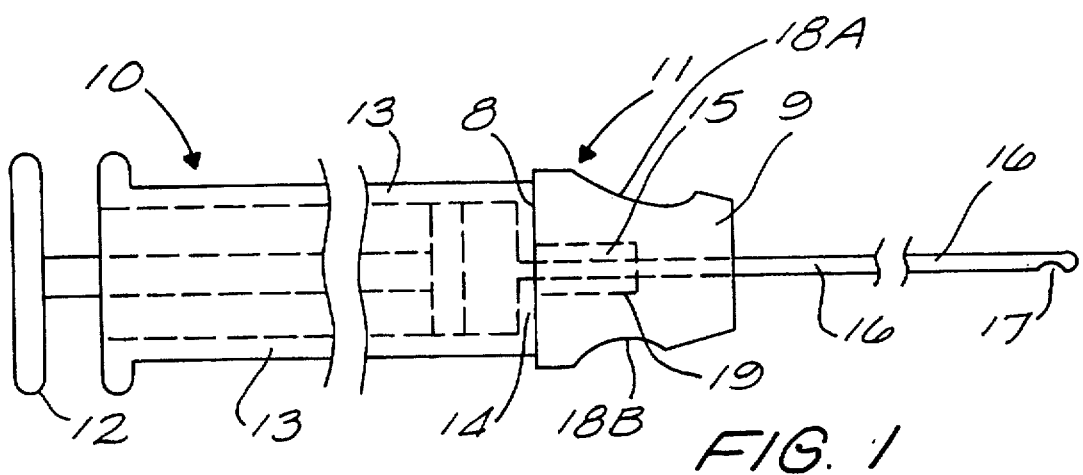

FIG. 1 is a side view of the preferred embodiment in conjunction with a syringe.

The barrel of syringe 10 is formed by wall 13 which forms a generally circular cross section. At one end of the barrel, is shoulder 14 which connects wall 13 with nozzle 15.

Nozzle 15 includes a channel which communicates with the interior of the barrel formed by wall 13. Plunger 12 is used to manually increase/decrease pressure to the interior cavity of the barrel of syringe 10.

Cannula 11 has a support member 9 and needle 16. Needle 16 is a hollow tube having an opening 17 which communicates through needle 16 to the channel within nozzle 15.

Support member 9 is structured such that a base member 8 presses against shoulder 14 so that forces are transferred longitudinally into wall 13 of syringe 10. Base member 8, in this preferred embodiment, has a diameter slightly larger than the diameter of the barrel of syringe 10. Ideally, no part of the support member extends past the shoulder 14 to contact an exterior surface of wall 13.

In the preferred embodiment of the invention, support is achieved via a precision fit between the support member 9 and the syringe nozzle 15. This fit provides not only additional support but also creates a seal for the fluids being injected or withdrawn.

Support member 9 is secured to nozzle 15 via a thread (not visible in this view) located along the interior wall 19 of the support member 9. This thread engages, and in the preferred embodiment, presses into the exterior surface of nozzle 15. This interaction between the support member 9 and nozzle 15 provides an exceptional securing action between the two.

Support member 9 further includes a thumb indentation 18A which is configured to receive the surgeon's thumb. Fore-finger indentation 18B is located on an opposing side for receipt of the surgeon's forefinger.

In the preferred embodiment, thumb indentation 18A is on a side opposing opening 17. Thus, thumb indentation 18A serves as an indicia for the surgeon giving the orientation of opening 17.

Thump indentation 18A and fore-finger indentation 18B provide for secure gripping of the assembly during use in an operation.

Figures 2A, 2B, 2C:
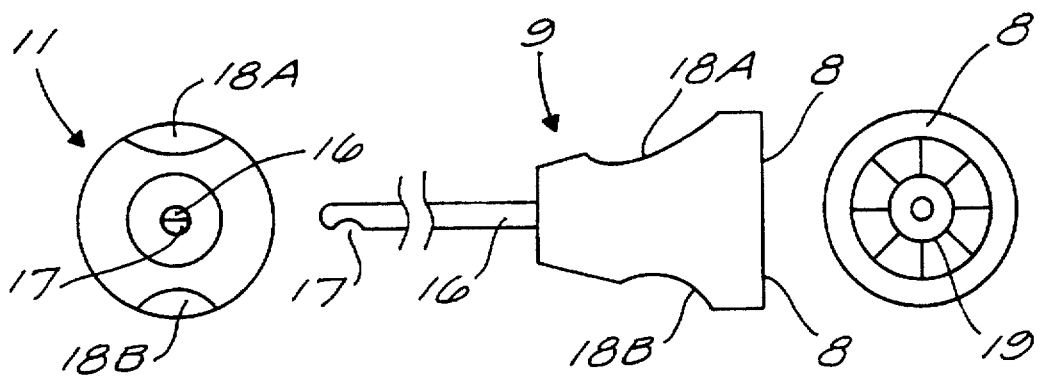

FIGS. 2A, 2B, and 2C are front, side, and end views respectively of the preferred embodiment.

Cannula 11 has needle 16 extending therefrom with an opening 17. Opening 17 communicates with an interior formed within wall member 19.

Base member 8 is adapted to transfer torque energy longitudinally into the wall of the syringe's barrel.

Figure 3:
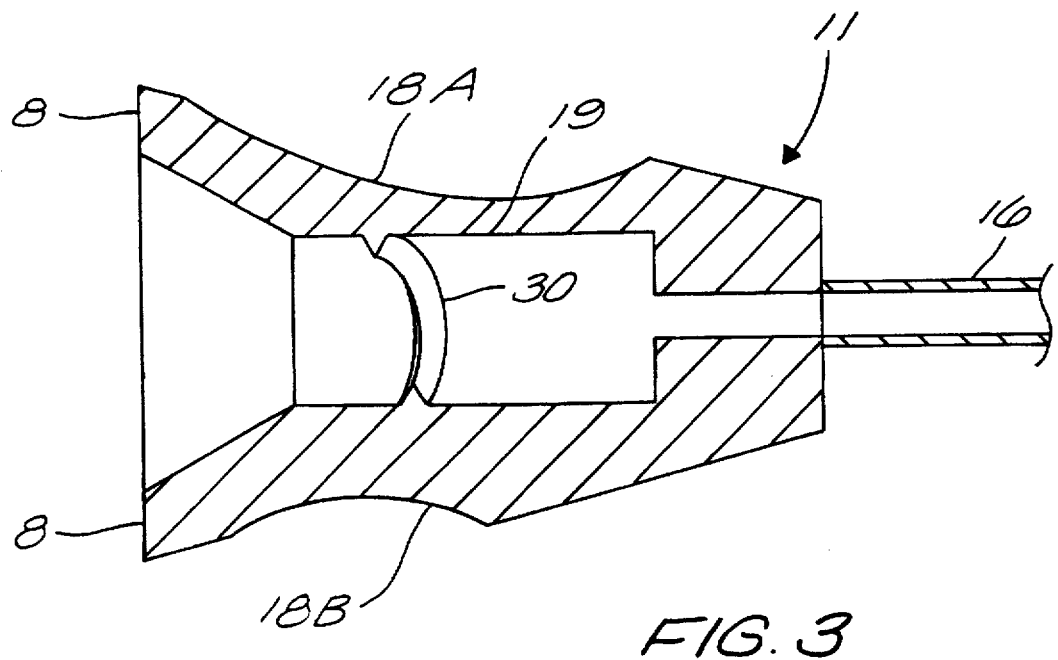
FIG. 3 is a cut-away view of the preferred embodiment.

FIG. 3 is a cut-away view of the preferred embodiment.

Base member 8 is designed to engage the syringe in such a manner that forces are transferred longitudinally into the wall of the barrel of the syringe.

Located along interior wall 19 is thread 30 which is adapted to engage an exterior portion of the nozzle of the syringe in such a manner that thread 30 forms a groove therein. Thread 30 is used in the preferred embodiment as a mechanism to secure cannula 11 to the syringe.

In the preferred embodiment, thread 30 is designed to fully secure the cannula 11 to the syringe with a quarter turn of the cannula relative to the syringe. This simple attachment mechanism provide for easy and convenient attachment of the cannula to the syringe and serves to properly seat cannula 11 to the syringe.

Figure 4:
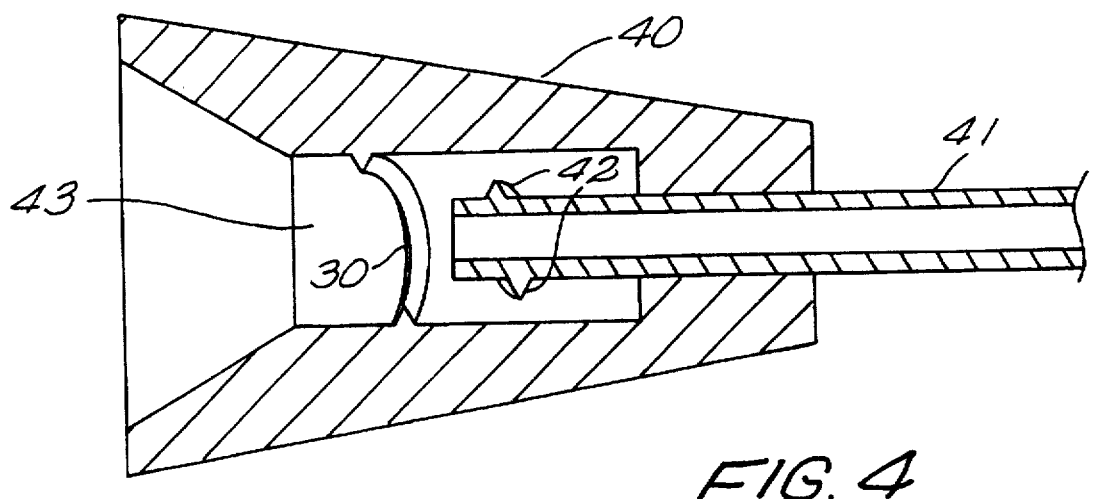
FIG. 4 is a cut-away view of an alternative embodiment of the invention.

FIG. 4 is a cut-away view of an alternative embodiment of the invention.

In this embodiment, cannula 40 has channel 43 which accepts the nozzle of the syringe (not shown). As described before, thread 30 is used to engage the outside of the syringe's nozzle; in this embodiment, thread 42, positioned on needle 41, simultaneously engages the interior portion of the nozzle.

In this manner, the nozzle of the syringe is affixed to the cannula both on the outside and the inside to provide exceptional locking therebetween.

Figure 5:
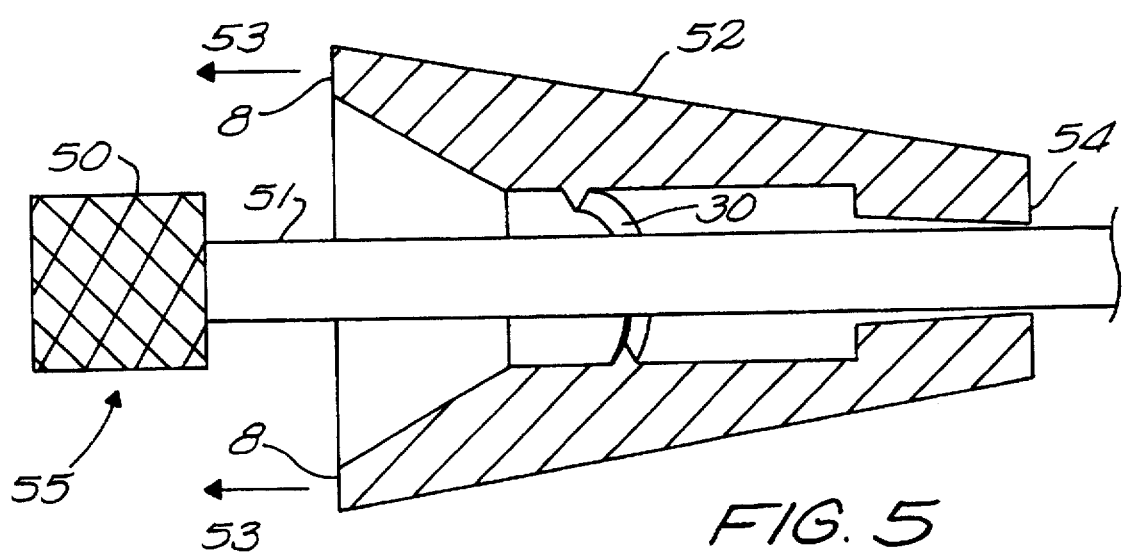
FIG. 5 is a cut-away view of an embodiment of the invention which is placed over an existing syringe needle.

FIG. 5 is a cut-away view of an embodiment of the invention which is placed over an existing syringe needle.

Syringe needle 55 has a luer-lock mechanism 54 and a needle portion 51. The luer-lock mechanism 54 is attached to the syringe's nozzle (not shown) and then the support member 52 is slid over needle 51, as indicated by arrows 53, so that needle 51 exits through shoulders 54.

Support member 52 is secured to the syringe's nozzle via thread 30. Shoulder 54 provides a structural connection between the support member 52 and the syringe needle 55 and gives excellent mechanical support for needle 51. This support is transferred readily to the syringe's wall member via base member 8.

Figure 6A:
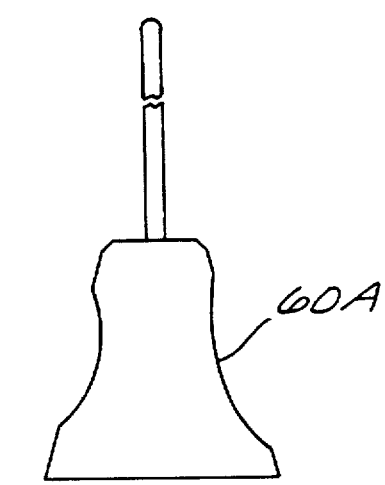
FIGS. 6A and 6B are side view of two embodiments of the invention.
Figure 6B:
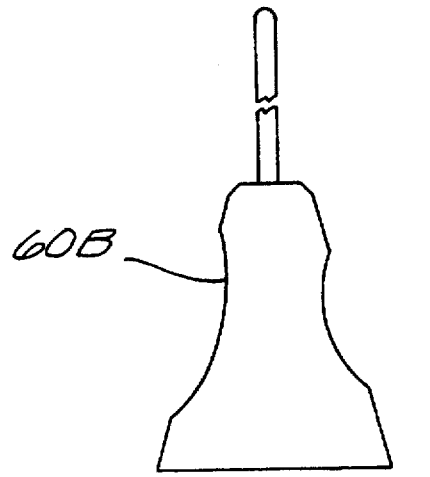

FIGS. 6A and 6B are side view of two embodiments of the invention.

As illustrated, cannula 60A is slightly shorter and more squat than cannula 60B. The various configurations are used to meet the needs of specific surgeon's with consideration given to ease in gripping and for the specific application.

The cannulas as described above are preferably manufactured from stainless steel, but, those of ordinary skill in the art readily recognize a variety of other materials which can be used including aluminum and plastics.

It is clear that the present invention creates a highly improved cannula capable of withstanding extra-ordinary torquing forces.

What is claimed is:

1. A cannula comprising:
   a) a connector member securable to a syringe and when secured to said syringe, is in contact exclusively with a lateral end and nozzle of said syringe and wherein said connector member is securable to an exterior portion of said nozzle of said syringe; and,
   b) a hypodermic needle having a hollow channel, said hypodermic needle connected to said connector member such that said hollow channel communicates with an interior channel in said nozzle of said syringe when said connector member is secured to said syringe.

2. The cannula according to claim 1, wherein said connector member includes an interior channel adapted to be connectable and releasable from an exterior surface of said nozzle of said syringe.

3. The cannula according to claim 2 wherein said interior channel of said connector member includes a thread adapted to engage the exterior surface of said nozzle of said syringe.

4. The cannula according to claim 3 wherein said thread is adapted to groove said exterior surface of said nozzle of said syringe.

5. The cannula according to claim 3 wherein said connector member includes fastening means for securing said connector to said syringe via an internal channel of said nozzle.

6. The cannula according to claim 5 wherein, during securement of said connector member to said syringe, said threads and said fastening means of said connector member engage the nozzle of the syringe substantially simultaneously.

7. The cannula according to claim 3 wherein said connector member is adapted such that said connector member does not extend over a barrel member of said syringe.

8. The cannula according to claim 3 wherein said connector member includes a generally circular base member having a diameter greater than a diameter of said barrel member of said syringe.

9. The cannula according to claim 8 wherein said base member of said connector member is adapted to be substantially at right angles to a wall forming the barrel of said syringe.

10. The cannula according to claim 9 wherein an exterior portion of said connector member is knurled to increase frictional contact between said connector member and a user's hand.

11. The cannula according to claim 3 wherein said hypodermic needle is removable from said connector member.

12. The cannula according to claim 11 wherein said hypodermic needle includes a luer-lock for engaging the interior channel of said nozzle of said syringe.

13. The cannula according to claim 1 wherein said hypodermic needle includes an opening disposed along a first side of said hypodermic needle, said opening communicating with the hollow channel within said hypodermic needle; and wherein said connector member includes an indicia disposed on a side opposing said first side of said hypodermic needle.

14. The cannula according to claim 13 wherein said indicia includes a thumb recess adapted to receive a user's thumb.

15. A surgical apparatus comprising:
   a) a syringe having,
      1) a wall member forming a hollow barrel,
      2) a lateral end member located at one end of said hollow barrel,
      3) a nozzle extending from said lateral end member and having an internal channel communicating with said hollow barrel, and,
      4) a plunger being extendable into said hollow barrel; and,
   b) a needle assembly having,
      1) a connector member in contact exclusively with the lateral end member of a syringe and to be secured to an exterior portion of the nozzle of said syringe, and,
      2) a hypodermic needle having a hollow channel, said hypodermic needle connected to said connector member such that said hollow channel communicates with the hollow barrel of said syringe via the interior channel in said nozzle of said syringe.

16. The surgical apparatus according to claim 15 wherein said connector member includes an interior channel adapted to connect with an exterior surface of said nozzle of said syringe.

17. The surgical apparatus according to claim 16 wherein said interior channel of said connector member includes a thread adapted to engage and groove the exterior surface of said nozzle of said syringe.

18. The surgical apparatus according to claim 17 wherein said connector member includes a generally circular base member having a diameter greater than a diameter of said barrel member of said syringe and adapted to be substantially at right angles to the wall member of said syringe.

19. The surgical apparatus according to claim 15 wherein said connector member includes fastening means for securing said connector to said syringe via an internal channel of said nozzle.

20. The surgical apparatus according to claim 19 wherein, during securement of said connector member to said syringe, said threads and said fastening means of said connector member engage the nozzle of the syringe substantially simultaneously.

21. The surgical apparatus according to claim 15 wherein said hypodermic needle includes an opening disposed along a first side of said hypodermic needle, said opening communicating with the hollow channel within said hypodermic needle; and wherein said connector member includes an indicia disposed on a side opposing said first side of said hypodermic needle.

22. The surgical apparatus according to claim 21 wherein said indicia includes a thumb recess adapted to receive a user's thumb.

23. A cannula comprising:
   a) a connector member having,
      1) an interior channel including a thread adapted to engage and groove an exterior surface of a nozzle of a syringe, and,
      2) a base member engaged exclusively to a lateral end of the syringe, said base member being substantially circular and having a diameter greater than a diameter of a barrel of the syringe; and,
   b) a hypodermic needle having a channel therein, said hypodermic needle connected to said connector member such that the channel of said hypodermic needle communicates with an interior channel in said nozzle of said syringe.

24. The cannula according to claim 23 wherein said base member of said connector member is adapted to be substantially at right angles to a wall forming the barrel of said syringe.

25. The cannula according to claim 23 herein said hypodermic needle includes an opening disposed along a first side of said hypodermic needle, said opening communicating with the hollow channel within said hypodermic needle; and wherein said connector member includes an indicia disposed on a side opposing said first side of said hypodermic needle.

26. The cannula according to claim 25 wherein said indicia includes a thumb recess adapted to receive a user's thumb.

\* \* \* \* \*